US008013119B2

(12) United States Patent
Nagai et al.

(10) Patent No.: US 8,013,119 B2
(45) Date of Patent: Sep. 6, 2011

(54) FLUORESCENT PROTEIN

(75) Inventors: Takeharu Nagai, Sapporo (JP); Atsushi Miyawaki, Wako (JP)

(73) Assignee: Riken, Saitama (JP)

( * ) Notice: Subject to any disclaimer, the term of this patent is extended or adjusted under 35 U.S.C. 154(b) by 40 days.

(21) Appl. No.: 11/719,166

(22) PCT Filed: Nov. 14, 2005

(86) PCT No.: PCT/JP2005/020843

§ 371 (c)(1),
(2), (4) Date: Feb. 9, 2009

(87) PCT Pub. No.: WO2006/051944

PCT Pub. Date: May 18, 2006

(65) Prior Publication Data

US 2009/0176211 A1 Jul. 9, 2009

(30) Foreign Application Priority Data

Nov. 15, 2004 (JP) ................................ 2004-330267

(51) Int. Cl.
*C07K 14/00* (2006.01)

(52) U.S. Cl. ......................................... 530/350; 436/86

(58) Field of Classification Search ........................ None
See application file for complete search history.

(56) References Cited

U.S. PATENT DOCUMENTS 7,226,993 B2 6/2007 Miyawaki et al.
7,247,449 B2 7/2007 Miyawaki et al.
7,345,157 B2 3/2008 Miyawaki et al.
2001/0003042 A1 6/2001 Lorens
2003/0004306 A1 1/2003 Miyawaki et al.
2005/0208624 A1 9/2005 Miyawaki et al.
2006/0275822 A1 12/2006 Miyawaki et al.
2007/0031912 A1 2/2007 Miyawaki et al.
2007/0292909 A1 12/2007 Miyawaki et al.

(Continued)

FOREIGN PATENT DOCUMENTS

JP 2002-512362 4/2002

OTHER PUBLICATIONS

Patterson et al. "A photoactivatable GFP for selective photolabeling of proteins and cells" Science (2002) vol. 297, 1873-1877.*

(Continued)

*Primary Examiner* — Nashaat Nashed
(74) *Attorney, Agent, or Firm* — Greenblum & Berstein, P.L.C.

(57) ABSTRACT

It is an object of the present invention to provide a fluorescent protein, which allows an acceptor for fluorescence resonance energy transfer (FRET) to appear in a stimulating light-dependent manner, thereby enabling the marking of any given cell organelle, cells, or tissues, with multiple colors. The present invention provides a fluorescent protein which consists of a fused protein of a donor fluorescent protein and an acceptor fluorescent protein, wherein before irradiation with stimulating light, the donor protein is able to emit fluorescence as a result of irradiation of the donor protein with excitation light; and after irradiation with stimulating light, intramolecular FRET occurs between the donor fluorescent protein and the acceptor fluorescent protein as a result of irradiation of the donor protein with excitation light, and the acceptor protein is able to emit fluorescence, and wherein the fluorescence of the donor protein and the fluorescence of the acceptor protein have wavelengths that are different from each other.

4 Claims, 4 Drawing Sheets

MSECFPΔC11 GT PA-GFPΔN3

U.S. PATENT DOCUMENTS

2008/0166799 A1 7/2008 Miyawaki et al.
2008/0227097 A1 9/2008 Miyawaki et al.
2008/0261257 A1 * 10/2008 Latz et al. ........................ 435/29
2009/0017516 A1 1/2009 Nagai et al.

OTHER PUBLICATIONS

Felber et al., "Evaluation of the CFP-substrate-YFP system for protease studies: advantages and limitations" *BioTechniques* 36(5):878-85, 2004.
Ando et al., "An optical marker based on the UV-induced green-to-red photoconversion of a fluorescent protein" *Proc. Natl. Acad. Sci.* 99(20):12651-56, 2002.
U.S. Appl. No. 10/575,900 to Miyawaki et al., entitled "Fluroescent Indicator Using FRET", which is the National Stage of PCT/JP2004/015671, filed Oct. 15, 2004.
U.S. Appl. No. 11/569,275 to Miyawaki et al., entitled "Fluroescent Protein", which is the National Stage of PCT/JP2005/009720, filed May 20, 2005.
Tsien, "The Green Fluorescent Protein" *Annu. Rev. Biochem*. 67:509-44, 1998.
Prasher et al., "Primary structure of the *Aequorea victoria* green-fluorescent protein" Gene 111:229-33, 1992.
Sawano et al., "Directed evolution of green fluorescent protein by a new versatile PCR strategy for site-directed and semi-random mutagenesis" *Nuc. Acids Res*. 28(16):e78, pp. i-vii, 2000.

* cited by examiner

Figure 1

| MSECFPΔC11 | GT | PA-GFPΔN3 |
|---|---|---|

[Figure 4]
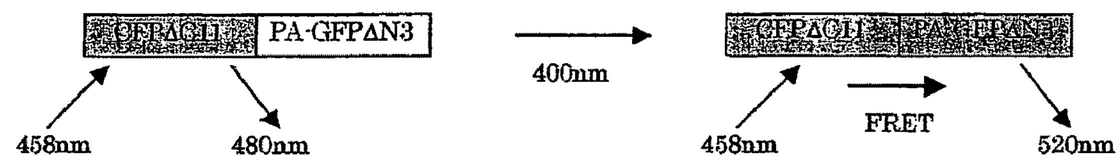

FLUORESCENT PROTEIN

TECHNICAL FIELD

The present invention relates to a novel fluorescent protein. More specifically, the present invention relates to a wavelength conversion-type fluorescent protein using fluorescence resonance energy transfer (FRET) that depends on light irradiation, and use thereof.

BACKGROUND ART

Green fluorescent protein (GFP) derived from a jellyfish, *Aequorea victoria*, has many purposes in biological research. Recently, various GFP mutants have been developed using random mutagenesis and semi-rational mutagenesis, wherein a color is changed, a folding property is improved, luminance is enhanced, or pH sensitivity is modified. Fluorescent proteins such as GFP can be fused with other proteins by recombinant DNA techniques to visualize the expression and translocation of the fusion proteins.

One of the most commonly used variants of GFP is yellow fluorescent protein (YFP). Among *Aequorea*-derived GFP mutants, YFP exhibits the fluorescence with the longest wavelength. The molar extinction coefficient ($\epsilon$) and fluorescence quantum yield ($\Phi$) of most YFPs are 60,000 to 100,000 $M^{-1}$ $cm^{-1}$ and 0.6 to 0.8, respectively (Tsien, R. Y. (1998). Ann. Rev. Biochem. 67, 509-544). These values are comparable to those of fluorescent compounds such as fluorescein and rhodamine. Cyan fluorescent protein (CFP) is another example of a GFP mutant. ECFP (enhanced cyan fluorescent protein) is such a CFP which has been known. Furthermore, red fluorescent protein (RFP) has been isolated from sea anemone (*Discoma* sp.), and among such red fluorescent proteins, DsRed has been known. Thus, four types of fluorescent proteins including green, yellow, cyan and red fluorescent proteins, have been developed one after another, and their spectrum range has been significantly extended.

In addition, using a fluorescent protein whose color is changed by light irradiation, it becomes possible to optically mark specific cells or organs. For such light irradiation-dependent marking of cells, tissues and the like, photoactivatable green fluorescent protein (PA-GFP) (Patterson G H and Lippincott-Schwartz J, Science 297, 1873-1877 (2002)) and Kaede (Ando R et al, Proc. Natl. Acad. Sci. USA 99, 12651-12656 (2002)) are used. However, since PA-GFP is characterized in that fluorescence appears from a nonfluorescent state, finding the position of a sample before irradiation with stimulating light is problematic. On the other hand, Kaede changes its color from green to red as a result of irradiation with stimulating light. However, Kaede requires excitation lights that depend on both colors, and thus the operation thereby becomes complicated. Moreover, since Kaede forms a tetramer, it is not suitable to observe dynamics of Kaede fused with any given protein.

DISCLOSURE OF THE INVENTION

Object to be Solved by the Invention

An object of the present invention is to provide a fluorescent protein, in which an acceptor for fluorescence resonance energy transfer (FRET) can be made to appear by irradiation with stimulating light, thereby enabling the marking of any given organelle, cells, or tissues, with multiple colors.

Means for Solving the Object

As a result of intensive studies directed towards achieving the aforementioned object, the present inventors have found that, when they fuse a donor fluorescent protein and an acceptor fluorescent protein, a fused fluorescent protein may be made, which is able to emit two types of fluorescence having different wavelengths. The fused fluorescent protein may also be configured to allow the donor fluorescent protein to emit fluorescence as a result of irradiation of the donor protein with excitation light. The fused fluorescent protein may also be configured to allow intramolecular FRET to occur between the donor fluorescent protein and the acceptor fluorescent protein as a result of irradiation of the donor fluorescent protein with excitation light and stimulation (photoconversion) of the acceptor protein with stimulating light, thereby changing the fluorescent spectrum of the fluorescent protein in a stimulating light-dependent manner. The present invention has been completed based on such findings.

That is to say, the present invention provides a fluorescent protein which consists of a fused protein of a donor fluorescent protein and an acceptor fluorescent protein, wherein before irradiation with stimulating light, the donor fluorescent protein is able to emit fluorescence as a result of irradiation of the donor fluorescent protein with excitation light; and after irradiation with stimulating light, intramolecular FRET occurs between the donor fluorescent protein and the acceptor fluorescent protein as a result of irradiation of the donor fluorescent protein with excitation light, and the acceptor protein is able to emit fluorescence. Furthermore, the present invention provides such a fluorescent protein, wherein the donor fluorescent protein and the acceptor fluorescent protein have wavelengths that are different from each other.

Preferably, the donor fluorescent protein is a CFP mutant, and the acceptor fluorescent protein is a PA-GFP mutant.

Preferably, the stimulating light is ultraviolet light or violet light.

Preferably, the donor fluorescent protein is a CFP mutant obtained by deletion of 11 amino acids at the C-terminus of CFP, and the acceptor fluorescent protein is a PA-GFP mutant obtained by deletion of 3 amino acids at the N-terminus of PA-GFP.

Preferably, the donor fluorescent protein is fused with the acceptor fluorescent protein via a linker sequence.

Preferably, the fluorescent protein of the present invention has either one of the following amino acid sequences:

(a) the amino acid sequence shown in SEQ ID NO: 2; and (b) an amino acid sequence comprising a deletion, substitution, and/or addition of one or several amino acids with respect to the amino acid sequence shown in SEQ ID NO: 2.

In another aspect, the present invention provides DNA encoding the aforementioned fluorescent protein of the present invention.

In a further aspect, the present invention provides a recombinant vector having the aforementioned DNA of the present invention.

In a further aspect, the present invention provides a transformant having the aforementioned DNA or recombinant vector of the present invention.

In a further aspect, the present invention provides a fusion fluorescent protein consisting of the aforementioned fluorescent protein of the present invention and another protein.

In a further aspect, the present invention provides a method of analyzing localization or kinetics of a protein in a cell, wherein the aforementioned fused fluorescent protein of the present invention is expressed in a cell.

In a further aspect, the present invention provides a fluorescent reagent kit which comprises the aforementioned fluorescent protein, DNA, recombinant vector, transformant, or fusion fluorescent protein of the present invention.

BEST EMBODIMENT FOR CARRYING OUT THE INVENTION

The embodiments of the present invention will be described in detail below.

(1) Fluorescent Protein of the Present Invention

The fluorescent protein of the present invention is a fluorescent protein which consists of a fused protein of a donor fluorescent protein and an acceptor fluorescent protein, wherein before irradiation with stimulating light, the donor fluorescent protein is able to emit fluorescence as a result of irradiation of the donor fluorescent protein with excitation light. After irradiation with stimulating light, intramolecular FRET occurs between the donor fluorescent protein and the acceptor fluorescent protein. The intramolecular FRET occurs as a result of irradiation of the donor fluorescent protein with excitation light, and the irradiation of the acceptor fluorescent protein with stimulating light. Furthermore, the present invention provides such a fluorescent protein, wherein the fluorescence of the donor protein and the fluorescence of the acceptor protein have wavelengths that are different from each other.

The combination of the donor fluorescent protein with the acceptor fluorescent protein, which is used in the present invention, is not particularly limited, as long as it achieves the aforementioned effect of the fluorescent protein of the present invention. Examples of such a donor fluorescent protein and an acceptor fluorescent protein that can be used herein include a cyan fluorescent protein (CFP), a yellow fluorescent protein (YFP), a green fluorescent protein (GFP), a red fluorescent protein (RFP), a blue fluorescent protein (BFP), and a mutant thereof.

The expression "a cyan fluorescent protein, a yellow fluorescent protein, a green fluorescent protein, a red fluorescent protein, a blue fluorescent protein, or a mutant thereof" is used in the present specification not only to mean known fluorescent proteins, but also to include all the mutants thereof (e.g. ECFP, EYFP, EGFP, ERFP, EBFP, etc. obtained by enhancing the fluorescence intensity of each of the aforementioned fluorescent proteins). For example, the gene of a green fluorescent protein has been isolated and sequenced (Prasher, D. C. et al. (1992), "Primary structure of the *Aequorea victoria* green fluorescent protein," Gene 111: 229-233). The amino acid sequences of a large number of other fluorescent proteins or mutants thereof have also been reported. Such amino acid sequences are described in Roger Y. Tsien, Annu. Rev. Biochem. 1998. 67: 509-44, and the documents cited therein, for example. As such, a green fluorescent protein (GFP), a yellow fluorescent protein (YFP), or a mutant thereof, including those derived from *Aequorea coerulescens* (e.g. *Aequorea victoria*) can be used, for example.

The nucleotide sequences of genes encoding the fluorescent proteins used in the present invention have been known. As such genes encoding the fluorescent proteins, commercially available products can also be used. For example, the EGFP vector, EYFP vector, ECFP vector, and EBFP vector, which are commercially available from Clontech, can be used as such gene products.

Examples of the combination of a fluorescent donor/a fluorescent acceptor that can be used in the present invention include: CFP or a mutant thereof/GFP or a mutant thereof; and BFP or a mutant thereof/GFP or a mutant thereof, but examples are not limited thereto. Preferably, a CFP mutant is used as a donor fluorescent protein, and a PA-GFP mutant is used as an acceptor fluorescent protein.

In the examples of the present invention, CFP and PA-GFP were used as a donor and an acceptor for FRET, respectively, so as to successfully produce a protein (Phamret) that changes its color from cyan to greenish yellow in a stimulating light-dependent manner. Specifically, a CFP mutant comprising a deletion of 11 amino acids at the C-terminus of CFP was used as a donor fluorescent protein, and a PA-GFP mutant comprising a deletion of 3 amino acids at the N-terminus of PA-GFP was used as an acceptor fluorescent protein.

In the case of the fluorescent protein of the present invention, before irradiation with stimulating light, a donor protein emits fluorescence as a result of irradiation of the donor protein with excitation light, and after irradiation with stimulating light, intramolecular FRET occurs between the donor fluorescent protein and the acceptor fluorescent protein as a result of irradiation of the donor fluorescent protein with excitation light, so that the acceptor fluorescent protein emits fluorescence. Stimulating light used herein is preferably ultraviolet light or violet light. The irradiation time of ultraviolet light or violet right is not particularly limited. Such ultraviolet light or violet right is applied for approximately several milliseconds to 10 minutes, for example.

In addition, the donor fluorescent protein may be fused with the acceptor fluorescent protein via a linker sequence. An example of such a linker sequence is an amino acid sequence consisting of several amino acids (e.g. approximately 1 to 5 amino acids).

Specific examples of the fluorescent protein of the present invention include:

(1) a fluorescent protein having the amino acid sequence shown in SEQ ID NO: 2; and (2) a fluorescent protein, which has an amino acid sequence comprising a deletion, substitution, and/or addition of one or several amino acids with respect to the amino acid sequence shown in SEQ ID NO: 2, and which consists of a fused protein of a donor fluorescent protein and an acceptor fluorescent protein, wherein before irradiation with stimulating light, the donor fluorescent protein is able to emit fluorescence as a result of irradiation of the donor fluorescent protein with excitation light, and after irradiation with stimulating light, intramolecular FRET occurs between the donor fluorescent protein and the acceptor fluorescent protein. The intramolecular FRET is a result of irradiation of the donor fluorescent protein with excitation light, so that the acceptor fluorescent protein is able to emit fluorescence. Furthermore, the present invention provides such a fluorescent protein, wherein the donor fluorescent protein and the acceptor fluorescent protein have wavelengths that are different from each other.

The range of "one or several amino acids" in the expression "an amino acid sequence comprising a deletion, substitution, and/or addition of one or several amino acids" used in the present specification is not particularly limited. For example, such a range means 1 to 20 amino acids, preferably 1 to 10 amino acids, more preferably 1 to 7 amino acids, further more preferably 1 to 5 amino acids, and particularly preferably about 1 to 3 amino acids.

In the case of the aforementioned fluorescent protein (Phamret) having the amino acid sequence shown in SEQ ID NO: 2, a CFP mutant comprising a deletion of 11 amino acids at the C-terminus of CFP was used as a donor fluorescent protein, and a PA-GFP mutant comprising a deletion of 3 amino acids at the N-terminus of PA-GFP was used as an acceptor fluorescent protein. Before irradiation with stimulating light (400 nm), the donor protein is able to emit fluorescence (480 nm) as a result of irradiation of the donor protein with excitation light (458 nm). After irradiation with stimulating light (400 nm), intramolecular FRET occurs between the donor fluorescent protein and the acceptor fluorescent protein [as a result of irradiation of the donor protein with excitation light (458 nm)], so that the acceptor fluorescent protein is able to emit fluorescence (520 nm).

A method of obtaining the fluorescent protein of the present invention is not particularly limited. The above fluorescent protein may be synthesized by chemical synthesis, or a recombinant protein produced by genetic recombination may also be used.

When such a recombinant protein is used, first, DNA encoding such a fluorescent protein should be obtained. The amino acid sequences and nucleotide sequences of various types of fluorescent proteins used as a donor fluorescent protein and an acceptor fluorescent protein have been known to persons skilled in the art. DNA encoding such fluorescent proteins can be obtained as commercially available products, or such DNA can be cloned by common genetic recombination techniques such as PCR. The thus obtained DNA encoding the donor fluorescent protein and the acceptor fluorescent protein are successively ligated to each other according to genetic recombination techniques, so as to construct DNA encoding the fluorescent protein of the present invention. By introducing such DNA into a suitable expression system, the fluorescent protein of the present invention can be produced. Expression of the fluorescent protein in such an expression system will be described later in the present specification.

(2) DNA of the Present Invention

The present invention provides DNA encoding the fluorescent protein of the present invention.

An example of DNA encoding the fluorescent protein having the amino acid sequence shown in SEQ ID NO: 2 is DNA having the nucleotide sequence shown in SEQ ID NO: 1. In addition, DNA which has a nucleotide sequence comprising a deletion, substitution, and/or addition of one or several nucleotides with respect to the nucleotide sequence shown in SEQ ID NO: 1, and encodes the fluorescent protein of the present invention having the features as described above in the present specification, may also be included in the scope of the present invention.

The range of "one or several nucleotides" in the expression "a nucleotide sequence comprising a deletion, substitution, and/or addition of one or several nucleotides" used in the present specification is not particularly limited. For example, such a range means 1 to 50 nucleotides, preferably 1 to 30 nucleotides, more preferably 1 to 20 nucleotides, further more preferably 1 to 10 nucleotides, and particularly preferably about 1 to 5 nucleotides.

The DNA of the present invention can be synthesized by the phosphoamidite method, for example. Otherwise, it can also be produced by polymerase chain reaction (PCR) using specific primers. A method of producing the DNA of the present invention or a fragment thereof is as described above in the present specification.

Moreover, a method of introducing a desired mutation into any given nucleic acid sequence has been known to persons skilled in the art. For example, DNA comprising a mutation can be constructed using, as appropriate, known techniques such as sited-directed mutagenesis, PCR using degenerate oligonucleotides, or a technique of exposing cells containing nucleic acids to a mutation-inducing agent or radioactive ray. Such known techniques are described, for example, in Molecular Cloning: A laboratory Manual, $2^{nd}$ Ed., Cold Spring Harbor Laboratory, Cold Spring Harbor, N.Y., 1989; and Current Protocols in Molecular Biology, Supplement 1 to 38, John Wiley & Sons (1987-1997).

(3) Recombinant Vector of the Present Invention

The DNA of the present invention can be inserted into a suitable vector and used. The type of vector used in the present invention is not particularly limited. For example, it may be either a vector that can autonomously replicate (e.g., a plasmid, etc.), or a vector that is incorporated into the genome of a host cell when it is introduced into the host cell and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows transcriptional activity in host cells, and it is appropriately selected depending on the type of host cell.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage lambda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Shizosaccharomyces*. Examples of such cells may include *Saccharomyces cerevisiae* and *Saccharomyces kluyveri*. Examples of a method of introducing a recombinant vector into yeast host cells may include electroporation, the spheroplast method, and the lithium acetate method.

Examples of other fungal cells may include those belonging to Filamentous fungi such as *Aspergillus, Neurospora, Fusarium* or *Trichoderma*. Where Filamentous fungi are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus that can infect insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: solvent extraction, the salting-out method using ammonium sulfate or the like, the desalting method, the precipitation method using an organic solvent, anion exchange chromatography using resins such as diethylaminoethyl (DEAE) sepharose, cation exchange chromatography using resins such as S-Sepharose FF (manufactured by Pharmacia), hydrophobic chromatography using resins such as butyl sepharose or phenyl sepharose, the gel filtration method using a molecular sieve, affinity chromatography, the chromatofocusing method, and electrophoresis such as isoelectric focusing.

(5) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or a recombinant protein produced by a gene recombination technique.

Where a recombinant protein is produced, it is necessary to obtain DNA encoding the protein. By the method as mentioned above, DNA encoding the fluorescent protein of the present invention can be obtained. Also, DNA fragments encoding a protein to be fused are obtained in the same manner as above. Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as microinjection. By observing the distribution of the fusion protein over time, targeting activity of the amino acid sequence to be tested can be detected in the cells.

The type of protein to be tested and with which the fluorescent protein of the present invention may be fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, or the fluorescent protein of the present invention can be introduced into cells by microinjection or the like. For example, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, or pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae, Escherichia coli* cells, or the like can be used. A vector can be introduced into host cells by common methods such as the calcium phosphate method or electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organelle as a protein X, the distribution and movement of such a protein with respect to a nucleus, a mitochondria, an endoplasmic reticulum, a Golgi body, a secretory vesicle, a peroxisome, etc., can be observed.

Moreover, for example, axis cylinders or dendrites of nerve cells show an extremely complicated change in impulses in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on the purpose. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used. A filter set can be appropriately selected depending on the fluorescence wavelength of a fluorescent protein. When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

(6) Kit of the Present Invention

The present invention provides a kit for analyzing the localization of intracellular components and/or analyzing physiologically active substances. The kit is characterized in that it comprises at least one of the following: the fluorescent protein, the fusion fluorescent protein, the DNA, the recombinant vector, or the transformant, which are described in the present specification. The kit of the present invention can be produced from commonly used materials that are known per se, by using common methods.

Reagents such as the fluorescent protein or the DNA are dissolved in an appropriate solvent, so that the reagents can be prepared in a form suitable for conservation. Water, ethanol, various types of buffer solution, etc. can be used as such a solvent.

The present invention will be further described in the following examples. However, the present invention is not limited by these examples.

EXAMPLES

Example 1

Construction of Phamret Gene

First, pEGFP-N1 (Clontech) and pECFP-N1 (Clontech) were used as templates, and 5'-ATTGGATCCCACCATGGTGAGCAAGGGCGAG-3' (SEQ ID NO: 3) and 5'-GCAGAATTCTTACTTGTACAGCTCGTCCATG-3' (SEQ ID NO: 4) were used as primers, so as to carry out PCR. Thereafter, the PCR product was cleaved with restriction enzymes BamHI and EcoRI, and the thus cleaved fragment was then inserted into the BamHI-EcoRI site of pRSETB, so as to construct EGFP/pRSETB and ECFP/pRSETB, respectively.

Subsequently, based on a publication by Patterson and Lippincott-Schwartz (Science 297, 1873-1877, 2002), a PA-GFP gene was constructed from an EGFP gene. In order to substitute the leucine at position 64 of the EGFP protein with phenylalanine, the threonine at position 65 with serine, the threonine at position 203 with histidine, and the alanine at position 206 with lysine, EGFP/pRSETB was used as a template, and the following 3 primers were used:

```
5'-GTGACCACCTTCAGCTACGGCGTG-3'     (SEQ ID NO: 5);

5'-TACCTGAGCCACCAGTCCGCC-3'        (SEQ ID NO: 6);

and

5'-TACCAGTCCAAGCTGAGCAAA-3'        (SEQ ID NO: 7).
```

Mutagenesis was carried out according to the method described in a publication by Sawano and Miyawaki (Nucleic Acids Res. 28: E78, 2000).

Subsequently, in order to improve the maturation efficiency of the ECFP protein and to prevent multimer formation, a gene encoding mSECFP, wherein serine at position 72 was substituted with alanine, serine at position 175 was substituted with glycine, and alanine at position 206 was substituted with lysine, was constructed. The same above method was applied. Using ECFP/pRSETB as a template, a mutation was introduced using the following primers:

```
5'-CAGTGCTTCGCCCGCTACCCC-3'       (SEQ ID NO: 8);

5'-GAGGACGGCGGCGTGCAGCTC-3'       (SEQ ID NO: 9);

and

5'-CACCAGTCCAAGCTGAGCAAA-3'       (SEQ ID NO: 10).
```

Subsequently, using mSECFP/pRSETB as a template, PCR was carried out with the following primers: 5'-ATTGGATCCCACCATGGTGAGCAAGGGCGAG-3' (SEQ ID NO: 3); and 5'-CGGGGTACCGGCGGCGGTCACGAACTCCAG-3' (SEQ ID NO: 11). Thereafter, the PCR product was cleaved with restriction enzymes BamHI and KpnI, and the cleaved fragment was then inserted into the BamHI-KpnI of pRSETB (mSEGFPdC11/pRSETB). Subsequently, using PA-GFP/pRSETB as a template, PCR was carried out with the following primers: 5'-CGGGGTACCAAGGGCGAGGAGCTGTTCACC-3' (SEQ ID NO: 12); and 5'-GCAGAATTCTTACTTGTACAGCTCGTCCATG-3' (SEQ ID NO: 4). Thereafter, the PCR product was cleaved with restriction enzymes KpnI and EcoRI, and the cleaved fragment was then inserted into the KpnI-EcoRI of mSEGFPdC11/pRSETB, so as to construct Phamret/pRSETB. The nucleotide sequence of the fluorescent protein of the present invention, Phamret, is shown in SEQ ID NO: 1 of the sequence listing, and the amino acid sequence thereof is shown in SEQ ID NO: 2 of the sequence listing.

In order to allow Phamret to express in mammalian cells, Phamret/pRSETB was cleaved with BamHI and EcoRI, and the cleaved fragment was then inserted into the BamHI-EcoRI site of pcDNA3, so as to construct Phamret/pcDNA3. The structure of Phamret is shown in FIG. 1.

Example 2

Production of Cultured Mammalian Cells which can Stably Express Phamret $1\times10^5$ HeLa S3 cells, which had been cultured on a 35-mm plastic plate, were transfected with 1 μg of Phamret/pcDNA3 according to the lipofection method. 24 hours later, the cells were dispersed by trypsinization and were then spread on a 10-cm plastic plate. 24 hours later, 500 μg/ml geneticin was added to the plate. 2 weeks later, fluorescent cell colonies were picked up, and they were then plated on a 35-mm plastic plate for proliferation. Thereafter, the cells were subjected to freezing preservation at −80° C. For such freezing preservation, a Cell Banker was used.

Example 3

Color Conversion of Phamret by Violet Light Irradiation

The frozen-preserved HeLa S3 cells which can stably express Phamret were melted, and they were then plated on a 10-cm plastic plate. 2 days later, the cells were dispersed by trypsinization, and $3\times10^5$ cells were then plated on a 35-mm glass bottom plate coated with collagen. 24 hours later, the medium was replaced with a Hank's balanced salt solution, and a color conversion experiment was then carried out under a microscope. An FV1000 confocal laser microscope manufactured by Olympus Corp. was used as a microscope, and PLANApo ×60 NA1.2 Water was used as objective lens. Phamret was excited with laser light (laser power: 2%) of 458-nm line (maximum output: 3 mW) of a multi-argon laser, so that two types of fluorescence, 470 to 500 nm (donor channel) and 510 to 560 nm (acceptor channel), were simultaneously obtained. Before irradiation with laser light of 405 nm, the fluorescence of the donor channel was strong (FIGS. 2A and 2D). In contrast, when the cytoplasm (○1) was irradiated with laser light of 405 nm (maximum output: 25 mW) at a laser power of 1.2%, the color of Phamret was rapidly changed, so that the fluorescence of the acceptor channel became stronger (FIGS. 2B and 2E). When the nucleus region (○2) of another cell was irradiated with 405-nm laser, only the nucleus region changed its color, and the fluorescence of the acceptor channel became stronger (FIGS. 2C and 2F). Although a localized portion of cytoplasm or a partial nucleus region was irradiated with light of 405 nm, the cytoplasm as a whole or the nucleus as a whole changed its color. This is because of dispersion of Phamret. In addition, since the molecular weight of Phamret is 60 Kda, and since this size is larger than the maximum molecular weight (50 Kda) that is capable of free dispersion through a nuclear pore, Phamret that has changed its color does not enter into the nucleus (FIG. 2E), or it does not discharge from the nucleus (FIG. 2F). From the above results, it was proved that intracellular compartments can be marked with Phamret.

Example 4

FRET Efficiency from mSECFP to PA-GFP in Phamret after Color Conversion

Spectra obtained before and after color conversion were measured using the wavelength-scanning function of FV1000, so as to quantitatively confirm that color conversion of Phamret by irradiation with light of 405 nm involves FRET from mSECFP to PA-GFP. For this measurement, violet light of 405 nm was applied to cells over 1 minute, so as to completely change the color. In the spectrum obtained before color conversion, the fluorescence from mSECFP was dominant (open circle of FIG. 3). In contrast, after color conversion, the fluorescence from PA-GFP became dominant (filled circle of FIG. 3). At that time, the fluorescence from mSECFP was reduced, and thus it became clear that FRET from mSECFP to PA-GFP occurred, and that the efficiency thereof was approximately 90%.

As described in Examples 1 to 4 above, in the case of Phamret (a protein produced by tandemly ligating CFP comprising a deletion of 11 amino acids on the C-terminal side and PA-GFP comprising a deletion of 3 amino acids on the N-terminal side via a KpnI site (Gly-Thr)), before irradiation with stimulating light (ultraviolet light or violet light) (for example, 400 nm), fluorescence (480 nm) is emitted from CFP by light excitation of 455 to 490 nm (for example, 458 nm). In contrast, after irradiation with stimulating light, PA-GFP is subjected to photo-conversion, and as a result, the excitation energy of CFP is transferred to PA-GFP via intramolecular fluorescence resonance energy transfer (intramolecular FRET), so that fluorescence (520 nm) can be seen from PA-GFP (FIG. 4).

INDUSTRIAL APPLICABILITY

The present invention made it possible not only to easily confirm the sample before irradiation with stimulating light, but also to observe the sample with only one excitation light. In addition, since the present fluorescent protein does not form a multimer, it became possible to more quantitatively carry out kinetic analysis by binding this protein with any given protein.

BRIEF DESCRIPTION OF THE DRAWINGS

Figure 1:
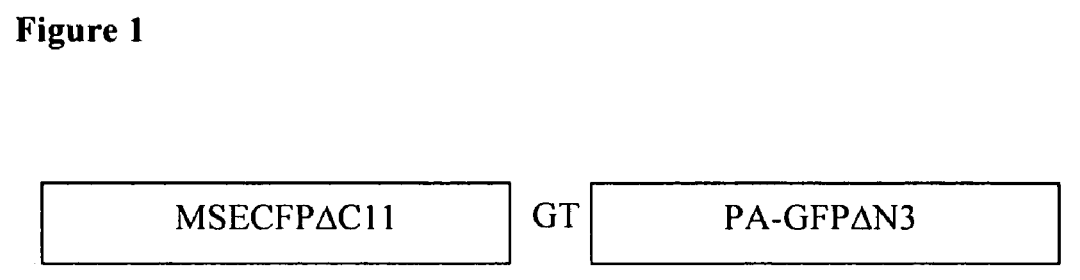

FIG. 1 is a schematic diagram showing the structure of Phamret.

FIG. 4 is a schematic diagram showing the structure and characteristics of Phamret.

The invention claimed is:

1. A fluorescent protein comprising:

a donor fluorescent protein fused via a linker sequence to an acceptor fluorescent protein, wherein the donor fluorescent protein and the acceptor fluorescent protein have fluorescence wavelengths that are different from each other; and wherein the fused fluorescent protein is configured to allow intramolecular fluorescence resonance energy transfer (FRET) to occur between the donor fluorescent protein and the acceptor fluorescent protein as a result of (a) photoactivation/photoconversion of the acceptor fluorescent protein with ultraviolet light or violet light of 400 or 405 nm, and (b) irradiation of the donor fluorescent protein with excitation light, wherein the donor fluorescent protein is a cyan fluorescent protein (CFP) mutant, the acceptor fluorescent protein is a photoactivatable green fluorescent protein (PA-GFP) mutant, and the fluorescent protein has either one of the following amino acid sequences:

(i) the amino acid sequence shown in SEQ ID NO: 2; or (ii) the amino acid sequence shown in SEQ ID NO: 2 in which one to ten amino acids have been deleted, substituted, and/or added.

2. A fusion fluorescent protein consisting of the fluorescent protein of claim 1 and another protein.

3. A method of analyzing localization or kinetics of a protein in a cell, wherein the fusion fluorescent protein of claim 2 is expressed in a cell.

4. A fluorescent reagent kit which comprises:

(i) the fluorescent protein of claim 1, or (ii) a fusion fluorescent protein consisting of the fluorescent protein of claim 1 and another protein.

* * * * *

SEQUENCE LISTING

<160> NUMBER OF SEQ ID NOS: 12

Figure 2:
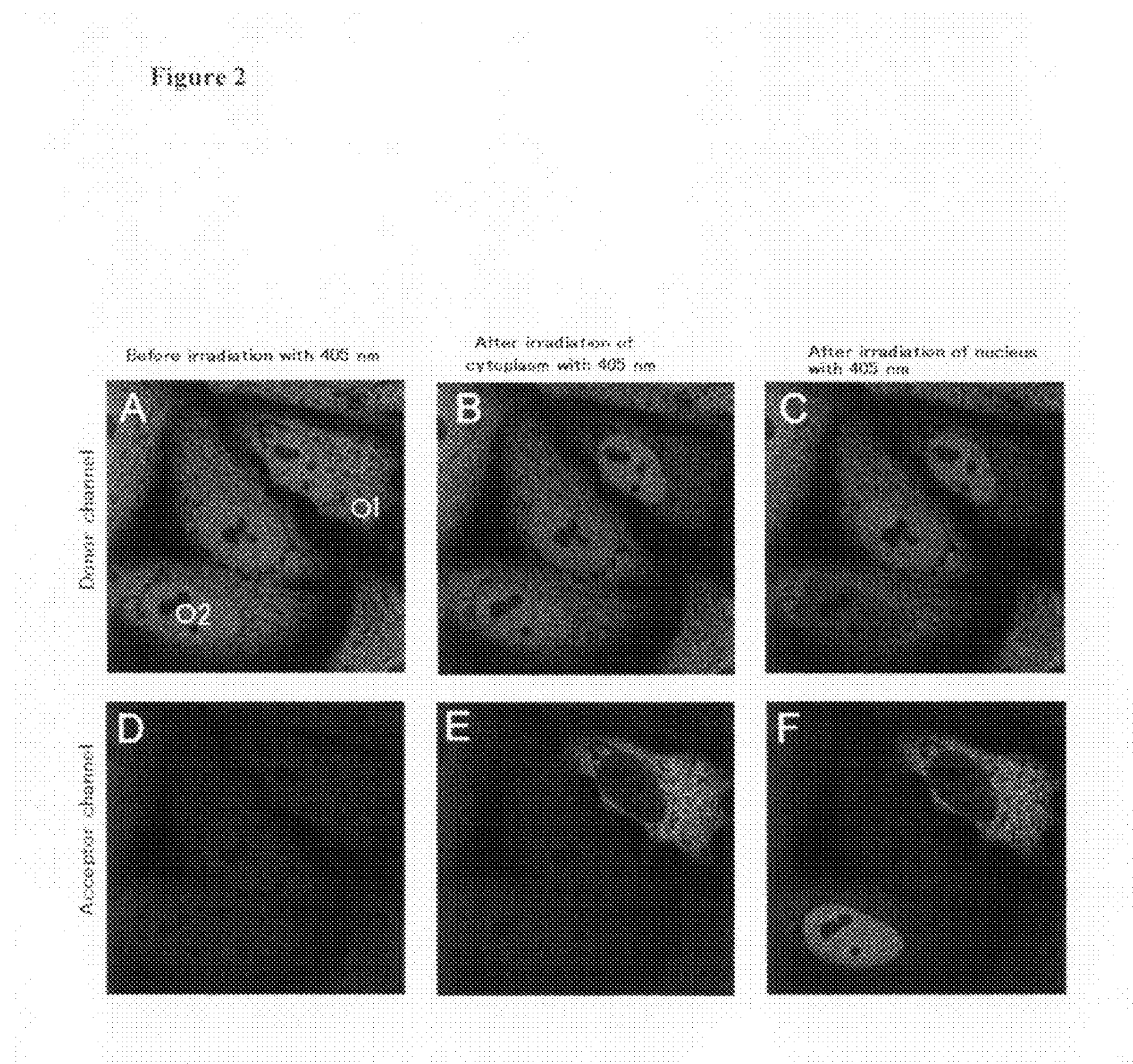
FIG. 2 shows color conversion of Phamret-expressing HeLa cells by light stimulation.
Figure 3:
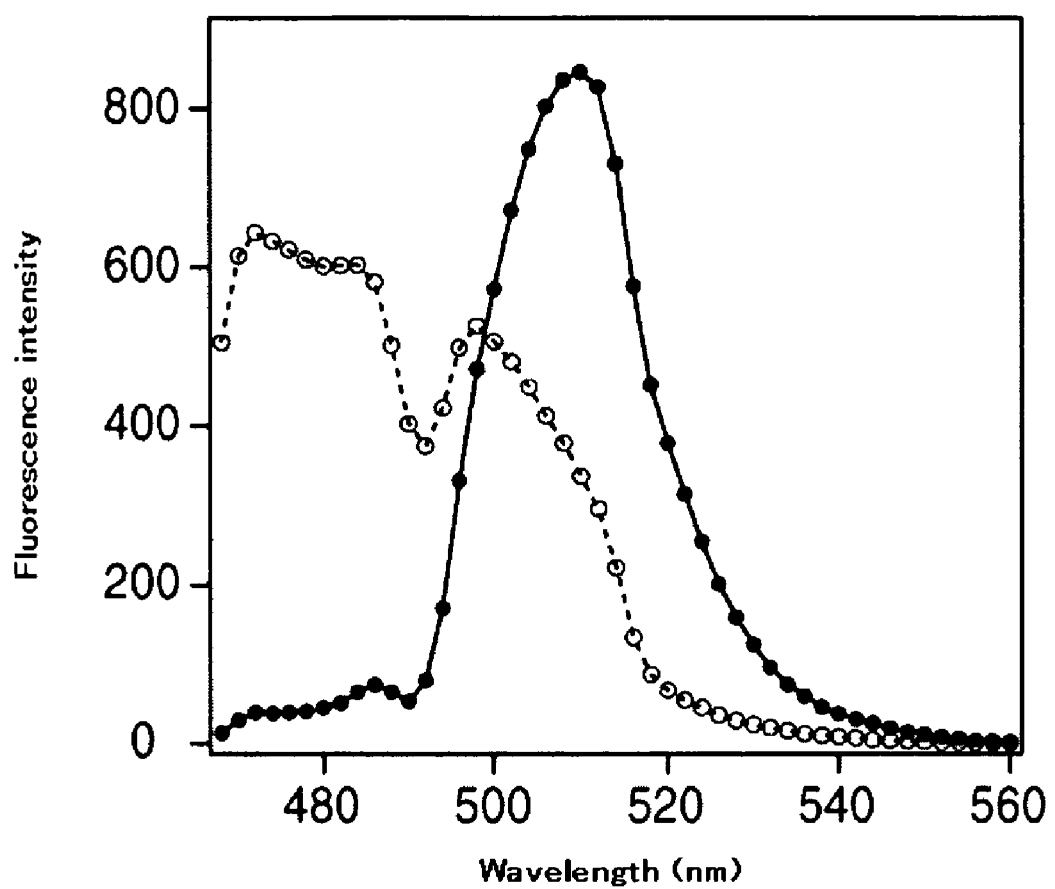
FIG. 3 is a spectrum obtained before and after color conversion of Phamret.

<210> SEQ ID NO 1
<211> LENGTH: 1401
<212> TYPE: DNA
<213> ORGANISM: Artificial Sequence
<220> FEATURE:
<223> OTHER INFORMATION: Description of Artificial Sequence: Synthetic recombinant DNA sequence
<220> FEATURE:
<221> NAME/KEY: CDS
<222> LOCATION: (1)..(1401)

<400> SEQUENCE: 1

```
atg gtg agc aag ggc gag gag ctg ttc acc ggg gtg gtg ccc atc ctg       48
Met Val Ser Lys Gly Glu Glu Leu Phe Thr Gly Val Val Pro Ile Leu
1               5                   10                  15

gtc gag ctg gac ggc gac gta aac ggc cac agg ttc agc gtg tcc ggc       96
Val Glu Leu Asp Gly Asp Val Asn Gly His Arg Phe Ser Val Ser Gly
            20                  25                  30

gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
        35                  40                  45

tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
    50                  55                  60

ctg acc tgg ggc gtg cag tgc ttc gcc cgc tac ccc gac cac atg aag      240
Leu Thr Trp Gly Val Gln Cys Phe Ala Arg Tyr Pro Asp His Met Lys
65                  70                  75                  80

cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                85                  90                  95

cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
            100                 105                 110

gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125

atc gac ttc aag gag gac ggc aac atc ctg ggg cac aag ctg gag tac      432
Ile Asp Phe Lys Glu Asp Gly Asn Ile Leu Gly His Lys Leu Glu Tyr
    130                 135                 140

aac tac atc agc cac aac gtc tat atc acc gcc gac aag cag aag aac      480
Asn Tyr Ile Ser His Asn Val Tyr Ile Thr Ala Asp Lys Gln Lys Asn
145                 150                 155                 160

ggc atc aag gcc cac ttc aag atc cgc cac aac atc gag gac ggc ggc      528
Gly Ile Lys Ala His Phe Lys Ile Arg His Asn Ile Glu Asp Gly Gly
                165                 170                 175

gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190

ccc gtg ctg ctg ccc gac aac cac tac ctg agc acc cag tcc aag ctg      624
Pro Val Leu Leu Pro Asp Asn His Tyr Leu Ser Thr Gln Ser Lys Leu
        195                 200                 205

agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220

gtg acc gcc gcc ggt acc aag ggc gag gag ctg ttc acc ggg gtg gtg      720
Val Thr Ala Ala Gly Thr Lys Gly Glu Glu Leu Phe Thr Gly Val Val
225                 230                 235                 240

ccc atc ctg gtc gag ctg gac ggc gac gta aac ggc cac aag ttc agc      768
Pro Ile Leu Val Glu Leu Asp Gly Asp Val Asn Gly His Lys Phe Ser
```

```
            245                 250                 255

gtg tcc ggc gag ggc gag ggc gat gcc acc tac ggc aag ctg acc ctg      816
Val Ser Gly Glu Gly Glu Gly Asp Ala Thr Tyr Gly Lys Leu Thr Leu
            260                 265                 270

aag ttc atc tgc acc acc ggc aag ctg ccc gtg ccc tgg ccc acc ctc      864
Lys Phe Ile Cys Thr Thr Gly Lys Leu Pro Val Pro Trp Pro Thr Leu
        275                 280                 285

gtg acc acc ttc agc tac ggc gtg cag tgc ttc agc cgc tac ccc gac      912
Val Thr Thr Phe Ser Tyr Gly Val Gln Cys Phe Ser Arg Tyr Pro Asp
    290                 295                 300

cac atg aag cag cac gac ttc ttc aag tcc gcc atg ccc gaa ggc tac      960
His Met Lys Gln His Asp Phe Phe Lys Ser Ala Met Pro Glu Gly Tyr
305                 310                 315                 320

gtc cag gag cgc acc atc ttc ttc aag gac gac ggc aac tac aag acc     1008
Val Gln Glu Arg Thr Ile Phe Phe Lys Asp Asp Gly Asn Tyr Lys Thr
                325                 330                 335

cgc gcc gag gtg aag ttc gag ggc gac acc ctg gtg aac cgc atc gag     1056
Arg Ala Glu Val Lys Phe Glu Gly Asp Thr Leu Val Asn Arg Ile Glu
            340                 345                 350

ctg aag ggc atc gac ttc aag gag gac ggc aac atc ctg ggg cac aag     1104
Leu Lys Gly Ile Asp Phe Lys Glu Asp Gly Asn Ile Leu Gly His Lys
        355                 360                 365

ctg gag tac aac tac aac agc cac aac gtc tat atc atg gcc gac aag     1152
Leu Glu Tyr Asn Tyr Asn Ser His Asn Val Tyr Ile Met Ala Asp Lys
    370                 375                 380

cag aag aac ggc atc aag gcc aac ttc aag atc cgc cac aac atc gag     1200
Gln Lys Asn Gly Ile Lys Ala Asn Phe Lys Ile Arg His Asn Ile Glu
385                 390                 395                 400

gac ggc acg gtg cag ctc gcc gac cac tac cag cag aac acc ccc atc     1248
Asp Gly Thr Val Gln Leu Ala Asp His Tyr Gln Gln Asn Thr Pro Ile
                405                 410                 415

ggc gac ggc ccc gtg ctg ctg ccc gac aac cac tac ctg agc cac cag     1296
Gly Asp Gly Pro Val Leu Leu Pro Asp Asn His Tyr Leu Ser His Gln
            420                 425                 430

tcc aag ctg agc aaa gac ccc aac gag aag cgc gat cac atg gtc ctg     1344
Ser Lys Leu Ser Lys Asp Pro Asn Glu Lys Arg Asp His Met Val Leu
        435                 440                 445

ctg gag ttc gtg acc gcc gcc ggg atc act ctc ggc atg gac gag ctg     1392
Leu Glu Phe Val Thr Ala Ala Gly Ile Thr Leu Gly Met Asp Glu Leu
    450                 455                 460

tac aag taa                                                         1401
Tyr Lys
465
```

<210> SEQ ID NO 2
<211> LENGTH: 466
<212> TYPE: PRT
<213> ORGANISM: Artificial Sequence
<220> FEATURE:
<223> OTHER INFORMATION: Description of Artificial Sequence: Synthetic recombinant fused fluorescent protein

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

```
Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Thr Lys Gly Glu Glu Leu Phe Thr Gly Val Val
225                 230                 235                 240

Pro Ile Leu Val Glu Leu Asp Gly Asp Val Asn Gly His Lys Phe Ser
                245                 250                 255

Val Ser Gly Glu Gly Glu Gly Asp Ala Thr Tyr Gly Lys Leu Thr Leu
            260                 265                 270

Lys Phe Ile Cys Thr Thr Gly Lys Leu Pro Val Pro Trp Pro Thr Leu
        275                 280                 285

Val Thr Thr Phe Ser Tyr Gly Val Gln Cys Phe Ser Arg Tyr Pro Asp
    290                 295                 300

His Met Lys Gln His Asp Phe Phe Lys Ser Ala Met Pro Glu Gly Tyr
305                 310                 315                 320

Val Gln Glu Arg Thr Ile Phe Phe Lys Asp Asp Gly Asn Tyr Lys Thr
                325                 330                 335

Arg Ala Glu Val Lys Phe Glu Gly Asp Thr Leu Val Asn Arg Ile Glu
            340                 345                 350

Leu Lys Gly Ile Asp Phe Lys Glu Asp Gly Asn Ile Leu Gly His Lys
        355                 360                 365

Leu Glu Tyr Asn Tyr Asn Ser His Asn Val Tyr Ile Met Ala Asp Lys
    370                 375                 380

Gln Lys Asn Gly Ile Lys Ala Asn Phe Lys Ile Arg His Asn Ile Glu
385                 390                 395                 400

Asp Gly Thr Val Gln Leu Ala Asp His Tyr Gln Gln Asn Thr Pro Ile
                405                 410                 415

Gly Asp Gly Pro Val Leu Leu Pro Asp Asn His Tyr Leu Ser His Gln
            420                 425                 430

Ser Lys Leu Ser Lys Asp Pro Asn Glu Lys Arg Asp His Met Val Leu
        435                 440                 445

Leu Glu Phe Val Thr Ala Ala Gly Ile Thr Leu Gly Met Asp Glu Leu
    450                 455                 460

Tyr Lys
465
```

```
<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

attggatccc accatggtga gcaagggcga g                                   31


<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gcagaattct tacttgtaca gctcgtccat g                                   31


<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

gtgaccacct tcagctacgg cgtg                                           24


<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

tacctgagcc accagtccgc c                                              21


<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

taccagtcca agctgagcaa a                                              21


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

cagtgcttcg cccgctaccc c                                              21


<210> SEQ ID NO 9
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

gaggacggcg gcgtgcagct c                                              21


<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

caccagtcca agctgagcaa a                                              21


<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

cggggtaccg gcggcggtca cgaactccag                                     30


<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

cggggtacca agggcgagga gctgttcacc                                     30
```